(12) United States Patent
Kapurniotu et al.

(10) Patent No.: US 7,342,091 B2
(45) Date of Patent: Mar. 11, 2008

(54) SOLUBLE CYCLIC ANALOGUES OF β AMYLOID PEPTIDE

(75) Inventors: Afroditi Kapurniotu, Aachen (DE); Jürgen Bernhagen, Aachen (DE); Herwig Brunner, Stuttgart (DE)

(73) Assignee: Fraunhofer-Gesellschaf zur Forderung der angewandten Forschung e.V, Munich (DE)

( * ) Notice: Subject to any disclaimer, the term of this patent is extended or adjusted under 35 U.S.C. 154(b) by 0 days.

(21) Appl. No.: 10/250,581

(22) PCT Filed: Dec. 21, 2001

(86) PCT No.: PCT/EP01/15181

§ 371 (c)(1), (2), (4) Date: Jan. 14, 2004

(87) PCT Pub. No.: WO02/055552

PCT Pub. Date: Jul. 18, 2002

(65) Prior Publication Data
US 2004/0116337 A1 Jun. 17, 2004

(30) Foreign Application Priority Data
Jan. 13, 2001 (DE) ................... 101 01 430

(51) Int. Cl.
- *A61K 38/12* (2006.01)
- *A61K 38/00* (2006.01)
- *A61K 51/00* (2006.01)
- *A61K 39/385* (2006.01)
- *G01N 33/567* (2006.01)
- *G01N 33/566* (2006.01)
- *G01N 33/53* (2006.01)

(52) U.S. Cl. ............. 530/317; 514/9; 514/12; 435/7.1; 435/7.92; 435/7.5; 436/503; 436/501; 436/547; 436/544; 436/545; 424/1.57; 424/1.69; 424/193.1

(58) Field of Classification Search ............. 530/300, 530/317, 323, 324
See application file for complete search history.

(56) References Cited

U.S. PATENT DOCUMENTS
5,854,204 A   12/1998   Findeis et al.

FOREIGN PATENT DOCUMENTS
| DE | 197 25 619 | 12/1998 |
|----|------------|---------|
| WO | WO 00/38618 | 7/2000 |
| WO | WO 01/34631 | 5/2001 |

OTHER PUBLICATIONS

Findeis, et al., " Modified-Peptide Inhibitors of Amyloid β-Peptide Polymerization," Biochemistry, vol. 38, No. 21, pp. 6791-6800, (1999).

Harkany, et al., "Neuroprotective Approaches in Experimental Models of β-Amyloid Neurotoxicity: Relevance to Alzheimer's Disease," Prog. Neuro-Psychopharmacol. & Biol. Psychiat., vol. 23, pp. 963-1008, (1999).

Hilbich, et al., "Substitutions of Hydrophobic Amino Acids Reduce the Amyloidogenicity of Alzheimer's Disease βA4 Peptides," J. Mol. Biol., No. 228, pp. 460-473 (1992).

*Primary Examiner*—Olga N. Chernyshev
(74) *Attorney, Agent, or Firm*—Dickstein Shapiro LLP

(57) ABSTRACT

The invention concerns a peptide having the biological activity of an inhibitor of amyloid formation and its diagnostic and medical use.

15 Claims, 3 Drawing Sheets

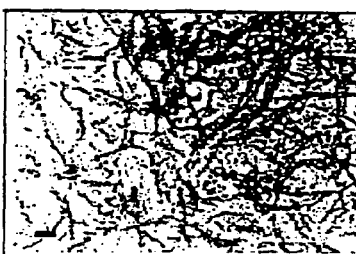

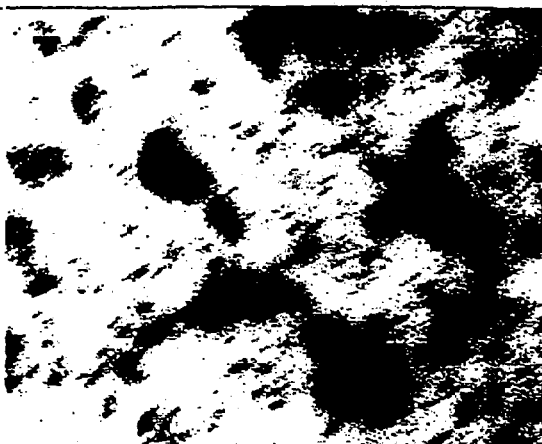

NH₂ -Asp-Ala-Glu-Phe-Arg-His-Asp-Ser-Gly-Tyr-Glu-
                                    17              21
Val-His-His-Gln-Lys-Leu-Val-Phe-Phe-Ala-Glu-

Asp-Val-Gly-Ser-Asn-Lys-COOH

Fig.3B

Cyclo-βAP(1-28)

```
         ᵋNH   ᵝCO
          |     |
         Lys   Asp
|―――――――――|―――――|―――――|
1         17    21    28
```

Control-βAP(1-28)

```
         ᵋNH₂  ᵝCOOH
          |     |
         Lys   Asp
|―――――――――|―――――|―――――|
1         17    21    28
```

SOLUBLE CYCLIC ANALOGUES OF β AMYLOID PEPTIDE

FIELD OF THE INVENTION

The present invention concerns peptides having the biological activity of a modulator of amyloidogenesis, process for discovering amyloidogenic peptides or their aggregates, pharmaceutical compositions for prophylaxis and therapy of diseases involving amyloidogenesis, and diagnostic compositions to detect such diseases.

BACKGROUND OF THE INVENTION

Amyloid diseases or amyloidoses are diseases involving amyloidogenesis, amyloid formation or aggregation of amyloid proteins in certain body tissues, often linked with cytotoxic effects. For instance, Alzheimer's disease involves amyloidogenesis of the β-amyloid peptide (β-AP).

It is assumed that the development of amyloid deposits of various peptides is responsible for occurrence and pathologic complications of amyloid diseases (Lorenzo et al., Nature 368 (1994), 756-760; Lorenzo et al., Proc. Nat'l. Acad. Sci. USA 91 (1994), 12243-12247; Lansbury et al., Proc. Nat'l. Acad. Sci. USA 96 (1999), 3342-3344; Koo et al., Proc. Nat'l. Acad. Sci. USA 96 (1999), 9989-9990; Sipe et al., Critical Reviews in Clinical Laboratory Sciences 31(4) (1994), 325-354. It is further assumed that inhibitors of amyloid formation are suitable pharmaceuticals for prophylaxis and treatment of the amyloid diseases.

Linear peptides of 3 to 15 amino acids which can act as agonists and/or inhibitors of amyloid formation are known from DE-A1 197 25 619. These peptides are distinguished by the fact that they contain at least the amino acids GA as the active sequence.

Peptides which modulate β-amyloid aggregation are known from U.S. Pat. No. 5,854,204. These are linearly constructed peptides of different lengths which are derived particularly from the β-amyloid precursor protein 770.

WO 96/39834 describes other linear peptides which can cure diseases with abnormal peptide aggregation. The peptides described have 3 to 15 amino acids, a hydrophobic segment of 3 amino acids and, in this hydrophobic segment, at least one amino acid which blocks a β-pleated sheet structure.

WO 96/07425 describes neurotoxic effects of the amyloid β-protein due to inhibiting synthetic peptides with linear structure. Diagnosis and treatment of Type II Diabetes mellitus using Amylin and derivatives of it is described n EP 0 289 287 and EP 0 309 100 A2.

Test procedures for early detection of amyloid diseases are not yet available, or are only in the development stage. That is because the problems of protein chemistry and technical analysis caused by amyloid formation have not yet allowed any analysis of amyloid formation. Because of that, the mechanism of amyloid formation is essentially unexplained. As a further result, there are not at present any pharmaceutical preparations for treatment of the amyloid diseases on the basis of modulators, especially inhibitors, of amyloidogenesis. Likewise, there are very few diagnostic procedures based on analysis of amyloid development, such as in vitro tests for evaluation of the kinetics, quantity and quality of formation of amyloid structures. The diagnosis still must be done symptomatically, as for Alzheimer's disease, for instance.

There is, in particular, need for suitable probes which can detect amyloid-forming peptides so as to determine abnormal increases in the concentration of amyloidogenic peptides among possible diseases. The problem for making such probes has been that the probes themselves must not aggregate, but still must interact specifically, i. e., bind, with the amyloidogenic peptides. The requirements for an inhibitor of amyloid formation will be similar. Also, such a substance obviously must not promote aggregation or aggregate itself, and it should also be able to bind the amyloidogenic peptides specifically to prevent further aggregation. It has not yet been possible to utilize any of the substances meeting the criteria listed above in medical diagnosis or therapy. There is, then, a great need for preparation of substances which can serve both as probes for diagnosis, particularly early detection, of diseases involving amyloid formation and for therapy, including prophylaxis, of such diseases.

BRIEF SUMMARY OF THE INVENTION

The present invention is, therefore, based on the technical problem of preparing substances which can serve both as probes for diagnosis of diseases involving amyloid formation and for therapy of such diseases.

BRIEF DESCRIPTION OF THE DRAWINGS

The invention is explained in more detail by means of examples, sequence records, and the accompanying figures.

FIGS. 1A to 1C and 2A and 2B show electron micrographs of the fibril-forming behavior of cβ-AP128 (SEQ ID NO: 2) (FIG. 1A), βAP (1-28) (SEQ ID NO: 20) (FIG. 1B), [Lys$^{17}$, Asp$^{21}$] β-AP (1-28) (linear control peptide) (SEQ ID NO: 21) (FIG. 1C) and β-AP (1-28) (SEQ ID NO: 20) (FIG. 2A) and a 1:1 mixtures of β-AP (1-28) (SEQ ID NO: 20) and cβ-AP128 (SEQ ID NO: 2) (FIG. 2B).

FIGS. 3A and 3B show schematically the structure of a peptide having an intramolecular bridge according to the invention and of the linear control peptide.

FIG. 3A shows β-AP(1-28) identified in SEQ ID NO: 20.

DETAILED DESCRIPTION OF THE INVENTION

The present invention solves the technical problem on which it is based by preparation of peptides with the biological activity of a modulator of amyloidogenesis, particularly an inhibitor of amyloidogenesis, this peptide being β-AP or a derivative of it, having at least one intramolecular bridge, and in particular at least one bridge between side chains of at least two amino acids in the peptide. In a particularly preferred embodiment of the present invention, the at least one bridge is formed by a covalent bond between side chains of at least two of the amino acids forming the peptide or amino acids introduced into the peptide (as substituents or added to the sequence). It can be provided that the bridge is formed by a direct bond between functional groups of the side chains, such as amino groups and carboxyl groups. However, it can also be provided that the side chains of the amino acids of the peptide involved in the bridging are covalently connected to each other through a spacer or linker, that is, an aminocarboxy, diamino or dicarboxy compound.

The aggregation and the amyloid formation which causes disease take place through formation of an intermolecular β-pleated sheet between the amyloidogenic peptide sequences which is necessary for development of intermolecular hydrogen bonds and hydrophobic interactions between the side chains of certain amino acid groups. This β-pleated sheet structure results in non-covalent bonding between initially two and then more amyloidogenic peptide chains, i. e., β-AP molecules, which then form insoluble aggregates, or amyloid structures.

Without the patent being bound to the theory, the intramolecular bridge in the β-AP provided according to the invention inhibits the biological activity of a modulator of amyloidogenesis, the transition between a disordered, α-helical conformation or a non-amyloidogenic state into an aggregated or a β-pleated sheet structure which can aggregate. According to the invention, introduction of the intramolecular bridge produces a conformation restriction, i. e., stabilization of a certain non-amyloidogenic state, such as the β-turn or the α-helix. Thus the cyclic peptides according to the invention are identical, or very similar, in their primary structure to the wild type molecules, the wild type β-AP, although there are major differences between these peptides and the native peptides with respect to their secondary structures. The conformation restriction of β-AP in a conformation which cannot aggregate, attained according to the invention, thus provides non-amyloidogenic molecules which act as aggregation inhibitors or inhibitors of amyloid development. They can, then, act as soluble agonists and probes of or for amyloid peptides. The cyclic peptides according to the invention are distinguished by the fact that on one hand, they cannot bind specifically covalently with, or associate specifically with, the native form, i. e., the wild type form, of the amyloid peptide on which their structure is based, and so can detect them. The peptides according to the invention are further distinguished by the fact that they themselves are not amyloidogenic and at the same time, they bind to the native form of the peptide, inhibiting binding to the native form of the peptide, inhibiting its association with other native peptides. In particular, binding of the cyclic peptides according to the invention occurs with soluble forms or monomers and oligomers of the native peptide which have not yet aggregated.

The cyclic peptides according to the invention also act as agonists, probes, and inhibitors of amyloid formation, which can be used for diagnosis and therapy of diseases involving amyloid formation. They can also be used as molecular tools for analysis and investigation of amyloidogenesis, as well as for research, development, and production of diagnostic and therapeutic agents for Alzheimer's disease, and for protection against Alzheimer's disease, and also as inoculants. The inhibition of the amyloidogenesis of the disease-causing peptides, produced according to the invention, simultaneously inhibits the cytotoxic action of the amyloid aggregate on tissue cells and eliminates another important pathogen. The cyclic peptides according to the invention can be produced at high purity by chemosynthesis using current methods of solid-phase peptide synthesis. They have high biological stability, especially stability to proteolysis, which can, for example, be further increased by incorporation of unnatural amino acids and ring structures. The cyclic peptides according to the invention can be handled easily. That is due to their high solubility, among other things. That contrasts with the difficulty of handling the native molecule, native β-AP. The cyclic peptides according to the invention further exhibit little if any side effects or antigenicity when used as therapeutic agents, because the inhibitors of amyloid formation have a primary structure which is very similar to the native peptides which occur in the body.

With respect to the present invention, a peptide is understood to be a molecule having at least two amino acids linked together through an amide bond, such as an oligopeptide, a polypeptide or a protein. The peptide can be a naturally occurring peptide, a chemically modified variant of one, or a peptide synthesized de novo. The peptide can have modifications, such as, for instance, glycosylations or other derivatizations such as alkylations, hydroxylations, aminations or the like. The peptide can be altered from the naturally occurring form, i. e., the native form, and so can represent a structural and/or functional equivalent such as a peptide analog or a peptide mimetic. These alterations can consist of insertions of amino acids, exchanges of amino acids, amino acid inversions, amino acid additions and/or amino acid deletions. The peptide can also contain unusual and/or unnatural amino acids. Likewise, the amino acids of the peptide can occur in the D- or L configuration.

In connection with the current invention, a peptide having the biological activity of a modulator of amyloidogenesis is understood to be a peptide which can influence peptides which form amyloid or amyloid-like structures with respect to their ability to aggregate into amyloids, particularly to promote, initiate or inhibit, for instance, to reduce or block amyloidogenesis. Promotion of the ability to aggregate can be desirable for research or for the deliberate tissue-specific localization of amyloids in tissues in which they are not harmful. A peptide having the biological activity of a modulator of amyloidogenesis is particularly distinguished by the fact that this peptide can interact with amyloidogenic peptides in such a way that their ability to aggregate is altered, and in particular, inhibited, especially with respect to the rate of aggregation, i.e., the velocity of aggregation, and the size or amount of the aggregates formed. This alteration of the aggregation ability occurs preferably by association or attachment, preferably through non-covalent bonding, to the preferably soluble form of the amyloidogenic peptide or to a soluble oligomer of the amyloidogenic peptide. In a particularly preferred embodiment of the present invention an inhibitory effect is an effect by which the lag phase of aggregation is extended, in comparison with the lag phase of only naturally occurring amyloidogenic peptides, by a factor of at least 1.5; 1.8; 2; 2.5; 3; 4; 5; 8; 10; 20; 40; 50; or 100. In a further embodiment of the invention there is an inhibitory effect if the degree of aggregation, compared with that of only naturally occurring amyloidogenic peptides or aggregates formed from them is reduced by 10, 20, 30, 40, 50, 60, 70, 80, 90 or 100%.

In connection with the present invention, the concept β-AP is understood to be a peptide having the biological activity of a modulator of amyloidogenesis, having an intramolecular bridge and primary structure identical to the wild type sequence, or a different primary structure, i. e., amino acid sequence. Commonly known test procedures, such as are described in U.S. Pat. No. 5,854,204, can be used to determine the modulation of amyloidogenesis, of the rate of aggregation, of the degree of aggregation (total amount of aggregation) and the velocity of or capability for aggregation. That patent, combined with the test procedures described there, are included in the disclosure of the present teaching.

In connection with the present invention, the concept "amino acids participating in bridge formation" is understood to mean those amino acids of the peptide, the side chains of which have the functional groups of which are directly or indirectly linked together to make a bond leading to the intramolecular bridge. Therefore the amino acids which participate in bridge formation have side chains with functional groups which either link directly with other functional groups of a different side chain of a different amino acid of the peptide, or their functional groups are linked with at least one spacer molecule which in turn is linked with the functional group of a side chain of another amino acid of the peptide which participates in the bridge formation. Such functional groups can, for instance, be hydroxy, amino, carboxy and/or thiol groups. The amino acids participating in the bridge formation can, naturally, be amino acids existing in the native sequence at this position. It is also possible according to the invention to introduce substituting amino acids which do not naturally occur at this site, or unnatural or unusual amino acids, by suitable substitutions of the naturally occurring amino acids. Those then are used for or involved in the bridge formation. Obviously it is also possible according to the invention for the amino acids participating in bridge formation also to be introduced into the amino acid sequence of the β-AP without a naturally occurring amino acid being deleted. Introduction of amino acids which do not occur naturally at this position can have the advantage that specific functional groups which allow or simplify bridge formation can be introduced deliberately at this position. One preferred embodiment of the invention provides for introduction into the amino acid sequence of amino acids which participate in bridge formation: Dab (2,4-diaminobutyric acid), Dap (2,3-diaminopropionic acid), Ser, Asp, Glu, Cys, Lys and/or Orn, such as by substitution or addition.

One advantageous development of the invention provides that the amino acids of the peptide which participate in bridge formation, preferably the two amino acids of the peptide which participate in bridge formation are arranged at relative separations of i+3, i+4, i+5, i+6 or i+7 in the peptide.

In one preferred embodiment of the present invention it is provided that the side chains of the amino acids of the peptide which participate in bridge formation are linked together by a spacer, with the spacer selected from the group consisting of X—$(CH_2)_n$—Y with n=1 to 6 and X/Y: $NH_2$/COOH or COOH/$NH_2$ or $NH_2$/$NH_2$ or COOH/COOH or OH/OH or SH/SH; or X is one of $NH_2$ or COOH or OH or SH, and Y is one of COOH or $NH_2$ or SH or OH. Obviously it is also possible to use other spacers. It is important according to the invention that that nature of X and Y, that is, of the terminal functional groups of the spacer or linker, be matched to the functional groups of the side chains being linked so that they can enter into a covalent chemical bond, such as by linking an amino group with a carboxyl group, or a carboxyl group with a hydroxyl group or two hydroxyl groups or two SH groups.

In another preferred embodiment the cyclic peptide of the present invention can have other functional groups which are not related to bridge formation but which serve, for instance, for immobilization on supports, interaction with other molecules, detection, or the like. Such groups can be functionalized alkyl groups, aromatic groups, glyco groups, lipid groups, cyclic, heterocyclic or polycyclic groups, biotin-containing groups, avidin-containing groups, streptavidin-containing groups or the like. Obviously it can also be provided that peptides of the present invention fuse with other peptides, polypeptides or proteins or fragments of them, for example, with wild type β-AP, or derivatives or fragments of it.

The peptides according to the invention can have marker groups, such as enzymes, prosthetic groups, fluorescent materials, radioactive materials or luminescent materials.

Horseradish peroxidase, alkaline phosphatase, β-galactosidase or acetylcholinesterase are examples of enzymes which can be used. Streptavidin/biotin and avidin/biotin are examples of prosthetic groups. Umbelliferone, fluorescein, fluorescein isothiocyanate, rhodamine, dichlorotriazinylaminofluorescein, dansyl chloride or phycoerythrin are examples of fluorescent material which can be used. Examples of radioactive materials which can be used include $^{14}C$, 123I, $^{124}I$, $^{125}I$, $^{131}I$, $^{99m}Tc$, $^{35}S$ or $^{3}H$.

The amino acid numberings and positions used in the present teaching refer to the sequence of the native wild type β-AP, as is described in Table 1 of Hilblich et al., (J. Mol. Biol. 228 (1992), 460-473. The contents disclosed in that publication are completely included in the disclosure of the present teaching with respect to the sequence of the amino acids of β-AP and its preparation, and it is clearly stated that protection for that is requested in the context of the invention. The numbering, according to current teaching, is always from the N terminus to the C terminus.

In another particularly preferred embodiment of the present invention, in which the original peptide, i. e., the stem peptide, is β-AP, the amino acids participating in bridge formation appear in the regions 15 to 24 of the β-AP. According to another preferred development of this embodiment which relates back to the β-AP stem peptide, the β-AP has 1 to 28 (β-AP 1-28 or β-AP128) (SEQ ID NO: 20), 1 to 40 (β-AP 1 to 40 or β-AP140), 1 to 42 (β-AP 1-42 or βAP142) or 1 to 43 (β-AP 1-43 or β-AP143) amino acids. In another preferred embodiment of the present invention the amino acids which participate in the bridge formation of the β-AP are those which are naturally there or are there for example as amino acids introduced by substitution, e.g., lysine and aspartic acids, for example, at positions 17 and 21.

In one particularly preferred embodiment of the present invention the invention concerns the cyclic peptide $cyclo^{17,21}$ [$Lys^{17}$, $Asp^{21}$] β-AP (1 to 28) (abbreviated as cβ-AP 128 or cβ-AP (1 to 28) (SEQ ID NO: 2).

In another preferred embodiment, the cyclic peptide is $cyclo^{17,21}$ [$Lys^{17}$, $Asp^{21}$] β-AP (1 to 40) (SEQ ID NO: 3).

In another preferred embodiment the cyclic peptide is $cyclo^{17,21}$ [$Lys^{17}$, $Asp^{21}$] β-AP (1 to 42) (abbreviated as cβ-AP 142) (SEQ ID NO: 4).

In one preferred embodiment the cyclic peptide is $cyclo^{17,21}$ [$Asp^{17}$ $Lys^{21}$] β-AP (1 to 28) (SEQ ID NO: 5).

In another preferred embodiment the cyclic peptide is $cyclo^{17,21}$ [$Asp^{17}$, $Lys^{21}$] β-AP (1 to 40) (SEQ ID NO: 6).

In another preferred embodiment the cyclic peptide is $cyclo^{17,21}$[$Asp^{17}$, $Lys^{21}$] β-AP (1 to 42) (SEQ ID NO: 7).

In another particularly preferred embodiment the cyclic peptide is $cyclo^{17,21}$ [$Asp^{17}$, $Orn^{21}$] β-AP (1 to 28) (Orn: ornithine) (SEQ ID NO: 8).

In another preferred embodiment the cyclic peptide is $cyclo^{17,21}$ [$Asp^{17}$, $Orn^{21}$] β-AP (1 to 40) (SEQ ID NO: 9).

In another preferred embodiment the cyclic peptide is $cyclo^{17,21}$ [$Asp^{17}$, $Orn^{21}$] β-AP (1 to 42) (SEQ ID NO: 10).

In a particularly preferred embodiment of the present invention the cyclic peptide is $cyclo^{17,21}$ [$Asp^{17}$, $Dab^{21}$] β-AP (1 to 28) (Dab: 2,4-diaminobutyric acid) (SEQ ID NO: 11).

In another preferred embodiment the cyclic peptide is $cyclo^{17,21}$ [$Asp^{17}$, $Dab^{21}$] β-AP (1 to 40) (SEQ ID NO: 12).

In another preferred embodiment the cyclic peptide is $cyclo^{17,21}$ [$Asp^{17}$, $Dab^{21}$] β-AP (1 to 42) (SEQ ID NO: 13).

In a particularly preferred embodiment of the present invention the cyclic peptide is $cyclo^{17,21}$ [$Orn^{17}$, Asp21] β-AP (1 to 28) (SEQ ID NO: 14).

In another preferred embodiment the cyclic peptide is $cyclo^{17,21}$[$Orn^{17}$, Asp21] β-AP (1 to 40) (SEQ ID NO: 15).

In another preferred embodiment the cyclic peptide is $cyclo^{17,21}$[$Orn^{17}$, $Asp^{21}$] β-AP (1 to 42) (SEQ ID NO: 16).

In another particularly preferred embodiment the cyclic peptide is cyclo$^{17,21}$[Dab$^{17}$, Asp$^{21}$] β-AP (1 to 28) (SEQ ID NO: 17).

In another preferred embodiment the cyclic peptide is cyclo$^{17,21}$[Dab$^{17}$, Asp$^{21}$] β-AP (1 to 40) (SEQ ID NO: 18).

In another preferred embodiment the cyclic peptide is cyclo$^{17,21}$[Dab$^{17}$, Asp$^{21}$] β-AP (1 to 42) (SEQ ID NO: 19).

The invention also concerns antibodies, especially monoclonal or polyclonal antibodies which can specifically recognize the cyclic peptide of the invention and bind to it. The antibodies can be modified in the usual manner, e. g., labeled. They can also occur in the immobilized form, on a carrier or fixed to beads.

The invention also provides for processes by which the peptides according to the invention are used as antigens to immunize human or animal organisms and the antibodies formed are obtained. Thus the invention also concerns processes for obtaining monoclonal and polyclonal antibodies in which the peptides according to the invention are used as antigens, particularly introduced into human or animal organisms and the antibodies formed after immunization are obtained or cells producing antibodies, such as spleen cells, are obtained to produce hybridoma cells producing monoclonal antibodies. Therefore the invention also concerns use of the peptides according to the invention to obtain monoclonal or polyclonal antibodies by means of processes which are themselves known. This can also involve recombinant processes, thus, for example, production of antibodies in *E. coli*. The antibodies obtained, which can, therefore, also be human or humanized antibodies, can be used for research, e.g., as a research tool, or for therapeutic or diagnostic purposes, especially for diagnosis and therapy of Alzheimer's disease. The polyclonal or monoclonal antibodies according to the invention can serve, for example, for analysis of the course of the disease in patients treated with peptides according to the invention, for instance, or for isolation and identification of other therapeutically effective peptides. The peptides according to the invention prove to be particularly advantageous with respect to their use as immunogens for production of antibodies for diagnostic and therapeutic purposes because of their substantially improved ease of handling compared with the naturally occurring poorly soluble analogs. The antibodies produced in this manner can in one embodiment detect specifically the peptides according to the invention and, in another embodiment, can also detect the native wild type β-AP present, possibly in the aggregated form, so that the antibodies according to the invention can, for instance, be used to diagnose Alzheimer's disease. The invention also concerns processes for immunizing human or animal organisms, by which the peptide according to the invention is applied to human or animal organisms and immunization is achieved against β-AP or its derivatives.

The peptides according to the invention can be synthesized and/or modified chemically in the usual manner. They can also be produced by recombinant DNA technology, or isolated from natural sources and modified.

The invention also concerns pharmaceutical compositions containing a cyclic peptide designated above in pharmaceutically active amount and in a pharmaceutically acceptable carrier. In one embodiment of the present invention, the pharmaceutical composition contains at least one cyclic peptide of the present invention in a prophylactically or therapeutically effective amount which is sufficient to alter, and in particular, to inhibit, aggregation, especially the rate of aggregation and/or the quantity of aggregate formed, or to alter native amyloid peptides, in particular, to inhibit them.

In another embodiment of the present invention, the pharmaceutical composition of the present invention has at least one cyclic peptide of the present invention in a prophylactically or therapeutically effective amount which is sufficient to alter, and in particular, to inhibit the neurotoxic effect of naturally occurring amyloidal peptides or their aggregates. The pharmaceutically active amount depends on various factors, such as the state of the disease, the size of the patient, the weight of the patient, the amount of endogenous amyloidal peptides present, etc.

Examples of pharmaceutically active carriers include solvents, dispersing agents, coatings, fillers, antibacterial and antifungal agents, isotonic agents, etc. Other additives can optionally be added, such as colorings or flavorings, emulsifiers, binders, release agents, etc.

Another embodiment of the present invention can provide for administering the pharmaceutical composition intravenously, orally, intraperitoneally, intraspinally, intracerebrally or intramuscularly. Provision can be made for administering the composition in the form of a sterile aqueous solution or dispersion, or a powder.

Provision can optionally be made for using other medically effective substances along with the cyclic peptide of the present invention in the pharmaceutical composition. Provision can be made for utilizing other substances in the pharmaceutical composition which serve, for instance, for transport in the target organism, e. g., through the blood-brain barrier.

In another preferred embodiment, the present invention concerns these diagnostic compositions containing at least one cyclic peptide of the present invention which preferably has a detection marker. Such a detection marker can be a radioactive label such as radioactive iodine or technetium. However, the detection marker can also be a fluorescent label, luminescent or enzyme label, or a spin label.

In another preferred embodiment, the invention concerns a process for detecting, especially screening, scanning or detecting, amyloidogenic peptides, especially β-AP or its derivatives, oligomers of amyloidogenic peptides or aggregates of amyloidogenic peptides, and of antibodies against such materials in a biological sample or an animal or human organism. In such a process at least one cyclic peptide of the present invention, preferably having a detection marker, or an antibody of the present invention with a detection marker as a probe is brought into contact with a sample being examined, preferably in a liquid, and an association of the peptide with amyloidogenic peptides, oligomers of them, aggregates of them, or antibodies against them is detected qualitatively and/or quantitatively. This process can be carried out in vitro in one embodiment of the present invention, and in vivo in another embodiment. Thus the concept of 'bringing into contact' includes incubation of the cyclic peptide with a sample in vitro or introduction on the cyclic peptide to a site in vivo where, for instance, natural amyloid peptide or its aggregate is present. Obviously, provision is also made to carry out this process in the presence of at least one other test substance such as native β-AP, other peptide variants, potential pharmaceuticals, potential diagnostic agents or marker substances in the form, for example, of competitive test procedures so that the effect of these other test substances on the aggregation behavior of natural β-AP and/or peptides according to the invention can be detected.

Provision can be made according to the invention for using the cyclic peptides in immobilized form. So provision can be made in a preferred manner to give the cyclic peptide other functional groups which make possible immobilization on solid carriers. The immobilization can, for instance, be done using the peptides according to the invention in antibody-based test, screening and analytical procedures, e. g., for identifying antibodies specific for β-AP or β-AP derivative. The immobilization can also be used for preparative processes in research and therapy such as for affinity matrices for binding, isolation, and depletion of amyloids from various liquids.

The invention also concerns the use of at least one cyclic peptide of the present invention for producing a medication of diseases characterized by amyloid development, i. e., amyloidoses, especially primary, secondary, inherited and/or isolated amyloidoses such as Alzheimer's disease, especially sporadic or familial Alzheimer's disease.

Therefore the invention also concerns processes for diagnosis and/or therapy, for instance, prophylaxis of amyloidoses, by which at least one cyclic peptide of the present invention is applied to a human or animal body or an isolated component of such a body in a pharmaceutically or diagnostically effective amount and, in the case of diagnostic use, bonding to amyloid structures is detected.

The invention also concerns processes for altering the aggregation of amyloidogenic peptides, oligomers or aggregates of them, or for inhibiting the cytotoxicity of amyloidogenic peptides, oligomers or aggregates of them, whereby peptides of the present invention are brought into contact, in vivo or in vitro with the amyloidogenic peptides, oligomers or aggregates of them and the aggregation behavior of the amyloidogenic peptides, oligomers or aggregates of them is altered, and especially the aggregation is reduced or inhibited. In the sense of the present invention, an amyloidosis is especially Alzheimer's disease.

The invention particularly concerns a process for modifying, preferably preventing, formation of aggregate from an amyloid β-AP contained in a liquid, whereby a peptide of the present invention is brought into contact with the liquid and incubated. This process can also serve for depleting or removing amyloid from liquid, e. g., body fluids.

The present invention also concerns kits comprising the cyclic peptides according to the invention and/or monoclonal or polyclonal antibodies directed against them, in which these agents can optionally be labeled.

Other advantageous embodiments of the invention arise from the sub-claims.

The sequence record which is part of the present teaching shows:

SEQ ID No. 1: the wild type amino acid sequence of β-AP (1-43),

SEQ ID NOs: 2-19: the amino acid sequences according to the invention, where there is in each case an intramolecular bridge between the side chains of the amino acids 17 and 21.

SEQ ID NO: 20: the wild type amino acid sequence of β-AP (1-28),

SEQ ID NO: 21: the linear control peptide of FIG. 3 bottom.

EXAMPLE 1

Preparation, Purification and Characterization of cβ-AP128 and Control β-AP (1-28)

The peptides were produced by current methods of solid-phase peptide synthesis using the Boc/Bzl synthesis strategy on PAM resin (Barany, G., Kneib-Cordonier, N. and Mullen, D. G. (1987), J. Pept. Res. 30, 705-739. They were removed from the resin with HF/anisole (10:1), and purified by preparative HPLC on a C18 column (Kapurniotu & Taylor (1995) J. Med. Chem. 38, 836-847). For the synthesis of cβ-AP128 (SEQ ID NO: 2), the side chains of $Lys^{17}$ and $Asp^{21}$ were protected by Fmoc or Fluorenyl-methyl ester (Ofm) protective groups, which were then removed selectively with 20% piperidine/DMF before forming the lactam bridge (Kapurniotu & Taylor, J. Med. Chem. 38, 836-847 (1995)). The side chain-to-side chain cyclization was done with benzotriazol-1-yloxy-tris-(dimethylamino)phosphonium hexafluorophosphate (BOP). It was tested for completeness with the Kaiser test (Kapurniotu & Taylor, J. Med. Chem. 38, 836-847 (1995)). In order to get a complete cyclization reaction, the cyclization reaction was done four times in mixtures of DMF, NMP and DMSO. (The duration of a cyclization was about 20 hours). The masses of the products purified by HPLC were determined by MALDI-MS, and their purity was verified by analytical HPLC.

EXAMPLE 2 cβ-AP128(SEQ ID NO: 2): Aggregation; testing of the fibril formation; testing of the inhibitory action on aggregation of β-AP (1-28) (SEQ ID NO: 21).

Physicochemical Properties of cβ-AP128 and Testing the Fibril Formation

The physicochemical properties of cβ-AP were investigated by FT-IR (Fourier-transform infrared spectrometry) and CD (circular dichroism spectropolarimetry). EM (electron microscopy) and AFM (atomic force microscopy) were used to test the properties of fibrils of cβ-AP128. In the EM studies, 450 μM solutions of cβ-AP128 or β-AP (1-28) (SEQ ID NO: 2) or [$Lys^{17}$, $Asp^{21}$] β-AP(1-28) (SEQ ID NO: 5) in 10 mM phosphate buffer, 150 mM NaCl and 30% acetonitrile, pH 5.5 were initially incubated for several days and tested for fibril formation. These studies showed that highly concentrated solutions of cβ-AP128 did not form any fibrils over many days (more than 30) (FIG. 1A). That is in contrast with the control peptides β-AP (1-28) (naturally occurring sequence) (SEQ ID NO: 20) and [$Lys^{17}$, $Asp^{21}$] β-AP (1-28) (linear control peptide) (SEQ ID NO: 21), which are completely fibrillated after three days incubation (FIGS. 1B, 1C).

FT-IR of the solutions/suspensions above showed that the bridging introduced in cβ-AP128 (SEQ ID NO: 2) prevents the β-pleated sheet conformation which native β-AP (SEQ ID NO: 20) and the control peptide [$Lys^{17}$, $Asp^{21}$] β-AP (1-28) (SEQ ID NO: 21) take on after aging, and thus inhibits aggregation and fibril formation.

FIG. 3A shows the native amino acid sequence of the β-AP fragment β-AP (1-28) (SEQ ID NO: 20). Positions 17 to 20 are emphasized to show their important role in the association and fibril formation. The upper part of FIG. 3B shows schematically the structure of the inventive β-AP (1-28) derivative $cyclo^{17,21}$[$Lys^{17}$, $Asp^{21}$] β-AP (1-28) (SEQ ID NO: 2), which is abbreviated 'cyclo-β-AP(1-28)' or called cβ-AP128, with the intramolecular bridge between the side chains of $Lys^{17}$ and $Asp^{21}$, particularly the ε-amino group of Lys and the β-carboxyl group of Asp. Therefore this example has an intramolecular bridge, in which the side chains of the amino acids at positions 17 and 21 are covalendy linked through a lactam bond, without intermediate linkers or spacers. The lower part of FIG. 3B shows the control peptide, control-β-AP(1-28), i. e., [$Lys^{17}$, Asp21] β-AP (1-28) (SEQ ID NO: 21). The figure makes it clear that replacement of the leucine at position 17 by lysine and of alanine at position 21 by aspartic acid yields analogs which differ from the native β-AP (1-28) (SEQ ID NO: 20) peptide and the covalent bonding of the side chains of these substituents, through the lactam bridge introduced between the ε-amino group and the β-carboxyl group, gives the structure according to the invention.

EXAMPLE 3

Inhibition of the Aggregation and Fibril Formation of β-AP (1-28) or [Lys$^{17}$, Asp$^{21}$] β-AP (1-28) by cβ-AP128

The effect of cβ-AP128 (SEQ ID NO: 20) on the aggregation and fibril formation of β-AP (1-28) was tested by CD and EM. A solution of 450 μM β-AP (1-28) (SEQ ID NO: 20) and cβ-AP128 (SEQ ID NO: 2) in 10 mM phosphate buffer, 150 mM NaCl and 30% acetonitrile, pH 5.5, was incubated for several days and tested for fibril formation by EM (FIGS. 2A and 2B). CD showed no changes of the CD spectra of these mixtures for more than 1 month, although β-AP (SEQ ID NO: 20) alone or [Lys$^{17}$, Asp$^{21}$] β-AP (1-28) (SEQ ID NO: 5) alone formed β-pleated sheets in less than 10 hours and then precipitated out as insoluble amyloid.

---

The invention claimed is:

1. Peptide with the biological activity of a modulator of amyloidogenesis wherein the peptide is a cyclic analog of β-amyloid peptide (β-AP) selected from the group consisting of peptides with amino acid sequences of SEQ ID NO: 2 to SEQ ID NO: 19, wherein the cyclic analog of β-amyloid peptide has at least one intramolecular bridge formed by covalent bonded side chains of at least two amino acids within the peptide sequence (bridge forming amino acids).

2. Peptide according to claim 1, characterized in that the analog is an inhibitor of amyloidogenesis.

3. Peptide according to claim 1, in which the side chains of the bridge forming amino acids are linked together directly or are linked through a spacer which is an aminocarboxy, diamino or dicarboxy compound.

4. Peptide according to claim 1, in which the amino acids which participate in bridge formation are the amino acids which occur naturally at the bridge formation positions of the peptide.

5. Peptide according to claim 1, in which at least one of the bridge forming amino acids which participate in bridge formation does not occur naturally at this position.

6. Peptide according to claim 1, in which the peptide further comprises at least one functional group selected from the group consisting of an alkyl group, functionalized alkyl group, aromatic group, oligopeptide, polypeptide, glyco group and lipid group.

7. Peptide according to claim 1, in which the peptide is immobilized on a carrier.

8. Pharmaceutical composition containing a peptide according to claim 1 and a pharmaceutically acceptable carrier.

9. Diagnostic composition containing a peptide according to claim 1 having a detection marker.

10. Process for decreasing the aggregation of amyloidogenic peptides present in a liquid under aggregation conditions, comprising bringing a peptide according to claim 1 into contact with the liquid and incubating the resulting liquid, wherein the aggregation is decreased as compared to the same conditions without the peptide of claim 1.

11. A method of making antibodies to amyloid, comprising administering a peptide according to claim 1 as an immunogen.

12. A method for the treatment of diseases during which amyloidogenesis occurs, comprising administering a peptide according to claim 1 to a human or animal body in an amount effective to reduce or block amyloidogenesis.

13. Diagnostic composition according to claim 9, in which the detection marker is a radioactive label, a fluorescent label, an enzyme label, a luminescence label or a spin label.

14. A method for the detection of amyloidogenic β-AP or an aggregate of the amyloidogenic β-AP comprising contacting a diagnostic composition according to claim 9 with a sample to be examined and determining whether binding of said peptide to said amyloidogenic β-AP or aggregate thereof has occurred by detecfing the marker which said peptide contains.

15. Process according to claim 10 in which the liquid is a body fluid.

* * * * *

UNITED STATES PATENT AND TRADEMARK OFFICE
CERTIFICATE OF CORRECTION

PATENT NO. : 7,342,091 B2  Page 1 of 1
APPLICATION NO. : 10/250581
DATED : March 11, 2008
INVENTOR(S) : Afroditi Kapurniotu et al.

It is certified that error appears in the above-identified patent and that said Letters Patent is hereby corrected as shown below:

On the Title Page item 73

(73) Please delete "Fraunhofer-Gesellschaf zur Forderung der angewandten Forschung e.V." and insert --Fraunhofer-Gesellschaft zur Förderung der angewandten Forschung e.V.--

Signed and Sealed this

Twenty-ninth Day of July, 2008

JON W. DUDAS
*Director of the United States Patent and Trademark Office*

SEQUENCE LISTING

```
<160> NUMBER OF SEQ ID NOS: 19

<210> SEQ ID NO 1
<211> LENGTH: 43
<212> TYPE: PRT
<213> ORGANISM: Homo sapiens

<400> SEQUENCE: 1

Asp Ala Glu Phe Arg His Asp Ser Gly Tyr Glu Val His His Gln Lys
  1               5                  10                  15

Leu Val Phe Phe Ala Glu Asp Val Gly Ser Asn Lys Gly Ala Ile Ile
             20                  25                  30

Gly Leu Met Val Gly Gly Val Val Ile Ala Thr
         35                  40

<210> SEQ ID NO 2
<211> LENGTH: 28
<212> TYPE: PRT
<213> ORGANISM: Homo sapiens
<220> FEATURE:
<221> NAME/KEY: PEPTIDE
<222> LOCATION: (17)..(21)
<223> OTHER INFORMATION: The side chains of the amino acids at positions
                        17 and 21 are linked together through an
                        intramolecular bridge.

<400> SEQUENCE: 2

Asp Ala Glu Phe Arg His Asp Ser Gly Tyr Glu Val His His Gln Lys
  1               5                  10                  15

Lys Val Phe Phe Asp Glu Asp Val Gly Ser Asn Lys
             20                  25

<210> SEQ ID NO 3
<211> LENGTH: 40
<212> TYPE: PRT
<213> ORGANISM: Homo sapiens
<220> FEATURE:
<221> NAME/KEY: PEPTIDE
<222> LOCATION: (17)..(21)
<223> OTHER INFORMATION: The side chains of the amino acids at positions
                        17 and 21 are linked together through an
                        intramolecular bridge.

<400> SEQUENCE: 3

Asp Ala Glu Phe Arg His Asp Ser Gly Tyr Glu Val His His Gln Lys
  1               5                  10                  15

Lys Val Phe Phe Asp Glu Asp Val Gly Ser Asn Lys Gly Ala Ile Ile
             20                  25                  30

Gly Leu Met Val Gly Gly Val Val
         35                  40
```

```
<210> SEQ ID NO 4
<211> LENGTH: 42
<212> TYPE: PRT
<213> ORGANISM: Homo sapiens
<220> FEATURE:
<221> NAME/KEY: PEPTIDE
<222> LOCATION: (17)..(21)
<223> OTHER INFORMATION: The side chains of the amino acids at positions
                        17 and 21 are linked together through an
                        intramolecular bridge.

<400> SEQUENCE: 4

Asp Ala Glu Phe Arg His Asp Ser Gly Tyr Glu Val His His Gln Lys
 1               5                  10                  15

Lys Val Phe Phe Asp Glu Asp Val Gly Ser Asn Lys Gly Ala Ile Ile
            20                  25                  30

Gly Leu Met Val Gly Gly Val Val Ile Ala
        35                  40

<210> SEQ ID NO 5
<211> LENGTH: 28
<212> TYPE: PRT
<213> ORGANISM: Homo sapiens
<220> FEATURE:
<221> NAME/KEY: PEPTIDE
<222> LOCATION: (17)..(21)
<223> OTHER INFORMATION: The side chains of the amino acids at positions
                        17 and 21 are linked together through an
                        intramolecular bridge.

<400> SEQUENCE: 5

Asp Ala Glu Phe Arg His Asp Ser Gly Tyr Glu Val His His Gln Lys
 1               5                  10                  15

Asp Val Phe Phe Lys Glu Asp Val Gly Ser Asn Lys
            20                  25

<210> SEQ ID NO 6
<211> LENGTH: 40
<212> TYPE: PRT
<213> ORGANISM: Homo sapiens
<220> FEATURE:
<221> NAME/KEY: PEPTIDE
<222> LOCATION: (17)..(21)
<223> OTHER INFORMATION: The side chains of the amino acids at positions
                        17 and 21 are linked together through an
                        intramolecular bridge.

<400> SEQUENCE: 6

Asp Ala Glu Phe Arg His Asp Ser Gly Tyr Glu Val His His Gln Lys
 1               5                  10                  15

Asp Val Phe Phe Lys Glu Asp Val Gly Ser Asn Lys Gly Ala Ile Ile
            20                  25                  30

Gly Leu Met Val Gly Gly Val Val
        35                  40

<210> SEQ ID NO 7
<211> LENGTH: 42
<212> TYPE: PRT
<213> ORGANISM: Homo sapiens
<220> FEATURE:
<221> NAME/KEY: PEPTIDE
<222> LOCATION: (17)..(21)
<223> OTHER INFORMATION: The side chains of the amino acids at positions
                        17 and 21 are linked together through an
                        intramolecular bridge.
```

-continued

```
<400> SEQUENCE: 7

Asp Ala Glu Phe Arg His Asp Ser Gly Tyr Glu Val His His Gln Lys
 1               5                  10                  15

Asp Val Phe Phe Lys Glu Asp Val Gly Ser Asn Lys Gly Ala Ile Ile
            20                  25                  30

Gly Leu Met Val Gly Gly Val Val Ile Ala
        35                  40

<210> SEQ ID NO 8
<211> LENGTH: 28
<212> TYPE: PRT
<213> ORGANISM: Homo sapiens
<220> FEATURE:
<221> NAME/KEY: PEPTIDE
<222> LOCATION: (21)
<223> OTHER INFORMATION: Xaa=Orn
<220> FEATURE:
<221> NAME/KEY: PEPTIDE
<222> LOCATION: (17)..(21)
<223> OTHER INFORMATION: The side chains of the amino acids at positions
                        17 and 21 are linked together through an
                        intramolecular bridge.

<400> SEQUENCE: 8

Asp Ala Glu Phe Arg His Asp Ser Gly Tyr Glu Val His His Gln Lys
 1               5                  10                  15

Asp Val Phe Phe Xaa Glu Asp Val Gly Ser Asn Lys
            20                  25

<210> SEQ ID NO 9
<211> LENGTH: 40
<212> TYPE: PRT
<213> ORGANISM: Homo sapiens
<220> FEATURE:
<221> NAME/KEY: PEPTIDE
<222> LOCATION: (21)
<223> OTHER INFORMATION: Xaa=Orn
<220> FEATURE:
<221> NAME/KEY: PEPTIDE
<222> LOCATION: (17)..(21)
<223> OTHER INFORMATION: The side chains of the amino acids at positions
                        17 and 21 are linked together through an
                        intramolecular bridge.

<400> SEQUENCE: 9

Asp Ala Glu Phe Arg His Asp Ser Gly Tyr Glu Val His His Gln Lys
 1               5                  10                  15

Asp Val Phe Phe Xaa Glu Asp Val Gly Ser Asn Lys Gly Ala Ile Ile
            20                  25                  30

Gly Leu Met Val Gly Gly Val Val
        35                  40

<210> SEQ ID NO 10
<211> LENGTH: 42
<212> TYPE: PRT
<213> ORGANISM: Homo sapiens
<220> FEATURE:
<221> NAME/KEY: PEPTIDE
<222> LOCATION: (21)
<223> OTHER INFORMATION: Xaa=Orn
<220> FEATURE:
<221> NAME/KEY: PEPTIDE
<222> LOCATION: (17)..(21)
<223> OTHER INFORMATION: The side chains of the amino acids at positions
                        17 and 21 are linked together through an
                        intramolecular bridge.
```

```
<400> SEQUENCE: 10

Asp Ala Glu Phe Arg His Asp Ser Gly Tyr Glu Val His His Gln Lys
 1               5                  10                  15

Asp Val Phe Phe Xaa Glu Asp Val Gly Ser Asn Lys Gly Ala Ile Ile
                20                  25                  30

Gly Leu Met Val Gly Gly Val Val Ile Ala
            35                  40

<210> SEQ ID NO 11
<211> LENGTH: 28
<212> TYPE: PRT
<213> ORGANISM: Homo sapiens
<220> FEATURE:
<221> NAME/KEY: PEPTIDE
<222> LOCATION: (21)
<223> OTHER INFORMATION: Xaa=Dab
<220> FEATURE:
<221> NAME/KEY: PEPTIDE
<222> LOCATION: (17)..(21)
<223> OTHER INFORMATION: The side chains of the amino acids at positions
                        17 and 21 are linked together through an
                        intramolecular bridge.

<400> SEQUENCE: 11

Asp Ala Glu Phe Arg His Asp Ser Gly Tyr Glu Val His His Gln Lys
 1               5                  10                  15

Asp Val Phe Phe Xaa Glu Asp Val Gly Ser Asn Lys
                20                  25

<210> SEQ ID NO 12
<211> LENGTH: 40
<212> TYPE: PRT
<213> ORGANISM: Homo sapiens
<220> FEATURE:
<221> NAME/KEY: PEPTIDE
<222> LOCATION: (21)
<223> OTHER INFORMATION: Xaa=Dab
<220> FEATURE:
<221> NAME/KEY: PEPTIDE
<222> LOCATION: (17)..(21)
<223> OTHER INFORMATION: The side chains of the amino acids at positions
                        17 and 21 are linked together through an
                        intramolecular bridge.

<400> SEQUENCE: 12

Asp Ala Glu Phe Arg His Asp Ser Gly Tyr Glu Val His His Gln Lys
 1               5                  10                  15

Asp Val Phe Phe Xaa Glu Asp Val Gly Ser Asn Lys Gly Ala Ile Ile
                20                  25                  30

Gly Leu Met Val Gly Gly Val Val
            35                  40

<210> SEQ ID NO 13
<211> LENGTH: 42
<212> TYPE: PRT
<213> ORGANISM: Homo sapiens
<220> FEATURE:
<221> NAME/KEY: PEPTIDE
<222> LOCATION: (21)
<223> OTHER INFORMATION: Xaa=Dab
<220> FEATURE:
<221> NAME/KEY: PEPTIDE
<222> LOCATION: (17)..(21)
<223> OTHER INFORMATION: The side chains of the amino acids at positions
                        17 and 21 are linked together through an
                        intramolecular bridge.
```

-continued

```
<400> SEQUENCE: 13

Asp Ala Glu Phe Arg His Asp Ser Gly Tyr Glu Val His His Gln Lys
 1               5                  10                  15

Asp Val Phe Phe Xaa Glu Asp Val Gly Ser Asn Lys Gly Ala Ile Ile
                20                  25                  30

Gly Leu Met Val Gly Gly Val Val Ile Ala
            35                  40

<210> SEQ ID NO 14
<211> LENGTH: 28
<212> TYPE: PRT
<213> ORGANISM: Homo sapiens
<220> FEATURE:
<221> NAME/KEY: PEPTIDE
<222> LOCATION: (17)
<223> OTHER INFORMATION: Xaa=Orn
<220> FEATURE:
<221> NAME/KEY: PEPTIDE
<222> LOCATION: (17)..(21)
<223> OTHER INFORMATION: The side chains of the amino acids at positions
                        17 and 21 are linked together through an
                        intramolecular bridge.

<400> SEQUENCE: 14

Asp Ala Glu Phe Arg His Asp Ser Gly Tyr Glu Val His His Gln Lys
 1               5                  10                  15

Xaa Val Phe Phe Asp Glu Asp Val Gly Ser Asn Lys
                20                  25

<210> SEQ ID NO 15
<211> LENGTH: 40
<212> TYPE: PRT
<213> ORGANISM: Homo sapiens
<220> FEATURE:
<221> NAME/KEY: PEPTIDE
<222> LOCATION: (17)
<223> OTHER INFORMATION: Xaa=Orn
<220> FEATURE:
<221> NAME/KEY: PEPTIDE
<222> LOCATION: (17)..(21)
<223> OTHER INFORMATION: The side chains of the amino acids at positions
                        17 and 21 are linked together through an
                        intramolecular bridge.

<400> SEQUENCE: 15

Asp Ala Glu Phe Arg His Asp Ser Gly Tyr Glu Val His His Gln Lys
 1               5                  10                  15

Xaa Val Phe Phe Asp Glu Asp Val Gly Ser Asn Lys Gly Ala Ile Ile
                20                  25                  30

Gly Leu Met Val Gly Gly Val Val
            35                  40

<210> SEQ ID NO 16
<211> LENGTH: 42
<212> TYPE: PRT
<213> ORGANISM: Homo sapiens
<220> FEATURE:
<221> NAME/KEY: PEPTIDE
<222> LOCATION: (17)
<223> OTHER INFORMATION: Xaa=Orn
<220> FEATURE:
<221> NAME/KEY: PEPTIDE
<222> LOCATION: (17)..(21)
<223> OTHER INFORMATION: The side chains of the amino acids at positions
                        17 and 21 are linked together through an
                        intramolecular bridge.
```

```
<400> SEQUENCE: 16

Asp Ala Glu Phe Arg His Asp Ser Gly Tyr Glu Val His His Gln Lys
  1               5                  10                  15

Xaa Val Phe Phe Asp Glu Asp Val Gly Ser Asn Lys Gly Ala Ile Ile
             20                  25                  30

Gly Leu Met Val Gly Gly Val Val Ile Ala
         35                  40

<210> SEQ ID NO 17
<211> LENGTH: 28
<212> TYPE: PRT
<213> ORGANISM: Homo sapiens
<220> FEATURE:
<221> NAME/KEY: PEPTIDE
<222> LOCATION: (17)
<223> OTHER INFORMATION: Xaa=Dab
<220> FEATURE:
<221> NAME/KEY: PEPTIDE
<222> LOCATION: (17)..(21)
<223> OTHER INFORMATION: The side chains of the amino acids at positions
                        17 and 21 are linked together through an
                        intramolecular bridge.

<400> SEQUENCE: 17

Asp Ala Glu Phe Arg His Asp Ser Gly Tyr Glu Val His His Gln Lys
  1               5                  10                  15

Xaa Val Phe Phe Asp Glu Asp Val Gly Ser Asn Lys
             20                  25

<210> SEQ ID NO 18
<211> LENGTH: 40
<212> TYPE: PRT
<213> ORGANISM: Homo sapiens
<220> FEATURE:
<221> NAME/KEY: PEPTIDE
<222> LOCATION: (17)
<223> OTHER INFORMATION: Xaa=Dab
<220> FEATURE:
<221> NAME/KEY: PEPTIDE
<222> LOCATION: (17)..(21)
<223> OTHER INFORMATION: The side chains of the amino acids at positions
                        17 and 21 are linked together through an
                        intramolecular bridge.

<400> SEQUENCE: 18

Asp Ala Glu Phe Arg His Asp Ser Gly Tyr Glu Val His His Gln Lys
  1               5                  10                  15

Xaa Val Phe Phe Asp Glu Asp Val Gly Ser Asn Lys Gly Ala Ile Ile
             20                  25                  30

Gly Leu Met Val Gly Gly Val Val
         35                  40

<210> SEQ ID NO 19
<211> LENGTH: 42
<212> TYPE: PRT
<213> ORGANISM: Homo sapiens
<220> FEATURE:
<221> NAME/KEY: PEPTIDE
<222> LOCATION: (17)
<223> OTHER INFORMATION: Xaa=Dab
<220> FEATURE:
<221> NAME/KEY: PEPTIDE
<222> LOCATION: (17)..(21)
<223> OTHER INFORMATION: The side chains of the amino acids at positions
                        17 and 21 are linked together through an
                        intramolecular bridge.
```

-continued

```
<400> SEQUENCE: 19

Asp Ala Glu Phe Arg His Asp Ser Gly Tyr Glu Val His His Gln Lys
 1               5                  10                  15

Xaa Val Phe Phe Asp Glu Asp Val Gly Ser Asn Lys Gly Ala Ile Ile
                20                  25                  30

Gly Leu Met Val Gly Gly Val Val Ile Ala
            35                  40
```